US009026193B2

(12) United States Patent
Pahlevan et al.

(10) Patent No.: US 9,026,193 B2
(45) Date of Patent: May 5, 2015

(54) INTRINSIC FREQUENCY HEMODYNAMIC WAVEFORM ANALYSIS

(71) Applicant: California Institute of Technology, Pasadena, CA (US)

(72) Inventors: Niema Pahlevan, Woodland Hills, CA (US); Peyman Tavallali, Pasadena, CA (US); Thomas Yizhao Hou, Arcadia, CA (US); Morteza Gharib, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/725,039

(22) Filed: Dec. 21, 2012

(65) Prior Publication Data

US 2013/0184573 A1    Jul. 18, 2013

Related U.S. Application Data

(60) Provisional application No. 61/579,456, filed on Dec. 22, 2011, provisional application No. 61/717,008, filed on Oct. 22, 2012, provisional application No. 61/739,880, filed on Dec. 20, 2012.

(51) Int. Cl.
*A61B 5/05*    (2006.01)
*A61B 5/00*    (2006.01)
(Continued)

(52) U.S. Cl.
CPC ............. *A61B 5/7282* (2013.01); *A61B 5/0004* (2013.01); *A61B 5/02405* (2013.01); *A61B 5/02416* (2013.01); *A61B 5/7278* (2013.01);
(Continued)

(58) Field of Classification Search
USPC ........................... 600/407–480; 382/128–132
See application file for complete search history.

(56) References Cited

U.S. PATENT DOCUMENTS 5,265,615 A * 11/1993 Frank et al. .................. 600/485
6,135,957 A   10/2000 Cohen-Bacrie et al.
(Continued)

FOREIGN PATENT DOCUMENTS

JP       2002-065677     3/2002
KR    10-2002-0055362    7/2002
(Continued)

OTHER PUBLICATIONS

Abbas, A. E., et al., "Echocardiographic Determination of Mean Pulmonary Artery Pressure", The American Journal of Cardiology, 2003, vol. 92, pp. 1373-1376.
(Continued)

*Primary Examiner* — Sanjay Cattungal
(74) *Attorney, Agent, or Firm* — One LLP

(57) ABSTRACT

Hardware and software methodology are described for cardiac health measurement. Hemodynamic waveforms variously acquired for a subject are analyzed to calculate or approximate intrinsic frequencies in two domains in two domains across the Dicrotic Notch. The intrinsic frequencies provide metrics/measures that correlate to the cardiac health of the subject. The systems may be used for monitoring a condition and/or is diagnosis. Exemplary uses include identifying (diagnosing) the presence of arrhythmia, heart failure, atrial fibrillation, aneurysms, vessel stenosis or aortic valve dysfunction and the necessity for valve replacement and/or monitoring congestive heart failure progression, together with identifying the acute need for hospitalization in connection with daily testing for any such condition.

30 Claims, 12 Drawing Sheets

(51) Int. Cl.
*A61B 5/024* (2006.01)
*A61B 8/02* (2006.01)
*A61B 8/08* (2006.01)
*A61B 8/00* (2006.01)
*A61B 5/02* (2006.01)
*A61B 8/06* (2006.01)

(52) U.S. Cl.
CPC . *A61B 5/746* (2013.01); *A61B 8/02* (2013.01); *A61B 8/5223* (2013.01); *A61B 8/565* (2013.01); *A61B 5/7235* (2013.01); *A61B 5/0077* (2013.01); *A61B 5/02028* (2013.01); *A61B 5/0507* (2013.01); *A61B 8/06* (2013.01)

(56) References Cited

U.S. PATENT DOCUMENTS

| | | | |
|---|---|---|---|
| 6,676,608 | B1 | 1/2004 | Keren |
| 6,738,734 | B1 | 5/2004 | Huang |
| 7,272,431 | B2 | 9/2007 | McGrath |
| 7,811,234 | B2 | 10/2010 | McGrath |
| 7,889,053 | B2 | 2/2011 | McGrath et al. |
| 8,232,866 | B2 | 7/2012 | McGrath et al. |
| 8,435,181 | B2 | 5/2013 | Yang et al. |
| 2003/0191400 | A1* | 10/2003 | Shalman et al. ............ 600/486 |
| 2007/0016031 | A1 | 1/2007 | Mourad et al. |
| 2007/0210786 | A1 | 9/2007 | Allen et al. |
| 2007/0238995 | A1* | 10/2007 | Sui et al. .................. 600/437 |
| 2009/0018422 | A1 | 1/2009 | Banet et al. |
| 2010/0185084 | A1 | 7/2010 | Zhang |
| 2011/0040181 | A1 | 2/2011 | Yokota et al. |
| 2011/0130800 | A1 | 6/2011 | Weinstein et al. |
| 2011/0224529 | A1 | 9/2011 | Lading |
| 2011/0275936 | A1 | 11/2011 | Cho et al. |
| 2012/0289848 | A1 | 11/2012 | Li et al. |

FOREIGN PATENT DOCUMENTS

| | | |
|---|---|---|
| KR | 10-2003-0070315 | 8/2003 |
| KR | 10-2006-0004931 | 1/2006 |
| WO | WO 2012/011029 | 1/2012 |
| WO | PCT/US2012/069947 | 2/2013 |
| WO | PCT/US2012/071452 | 3/2013 |
| WO | PCT/US2013/053068 | 11/2013 |
| WO | PCT/US2013/054529 | 11/2013 |
| WO | PCT/US2012/069947 | 6/2014 |
| WO | PCT/US2012/071452 | 6/2014 |

OTHER PUBLICATIONS

Angtuaco, M. J., et al., "Noninvasive Estimation of Diastolic Pulmonary Artery Pressure by Doppler Analysis of Tricuspid Regurgitation Velocity in Pediatric Patients", Congent. Heart Dis., 2011, pp. 1-8.

Cremer, A., et al., "Determination of central blood pressure by a noninvasive method (brachial BP and QKD interval)", J. Hypertens., 2012, vol. 30, pp. 1-7.

Feng, J., et al., "Determination of wave speed and wave separation in the arteries using diameter and velocity", Journal of Biomechanics, 2010, vol. 43, pp. 455-462.

Fletcher, R. R., et al., "Clip-on wireless wearable microwave sensor for ambulatory cardiac monitoring", IEEE, 2010, pp. 365-369.

Friedberg, M. K., et al., "A Novel Echocardiographic Doppler Method for Estimation of Pulmonary Arterial Pressures", J. Am. Soc. Echocard., 2006, pp. 559-562.

Greenfiled, Jr., J. C., et al., "Relation between pressure and diameter in main pulmonary artery of man", J. Appl. Physiol., 1963, vol. 18, No. 3, pp. 557-559.

Lanzarini, L., et al., "Noninvasive estimation of both systolic and diastolic pulmonary artery pressure from Doppler analysis of tricuspid regurgitant velocity spectrum in patients with chronic heart failure", American Heart Journal, 2002, vol. 144, pp. 1087-1094.

Lee, J. Y., et al., "A Microprocessor-Based Noninvasive Arterial Pulse Wave Analyzer", IEEE Transactions on Biomedical Engineering, 1985, vol. BME-32, No. 6, pp. 451-455.

Milan, A., et al., "Echocardiographic Indexes for the Non-Invasive Evaluation of Pulmonary Hemodynamics", J. Am. Soc. Echocard., 2010, vol. 23, No. 3, pp. 225-239.

Patel, D. J., et al., "Mechanical properties and dimensions of the major pulmonary arteries", J. Appl. Physiol., 1960, vol. 15, No. 1, pp. 92-96.

Selton-Suty, C., et al., "Non-invasive investigations of the right heart: How and why?", Archives of Cardiovascular Disease, 2009, vol. 102, pp. 219-232.

* cited by examiner

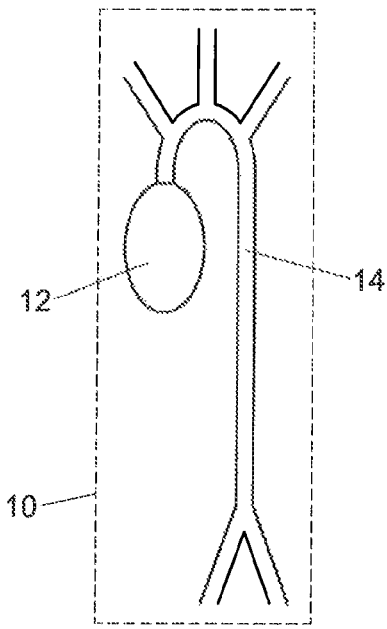
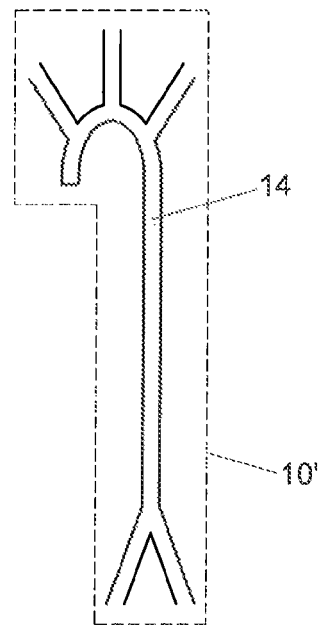
Fig. 1A    Fig. 1B
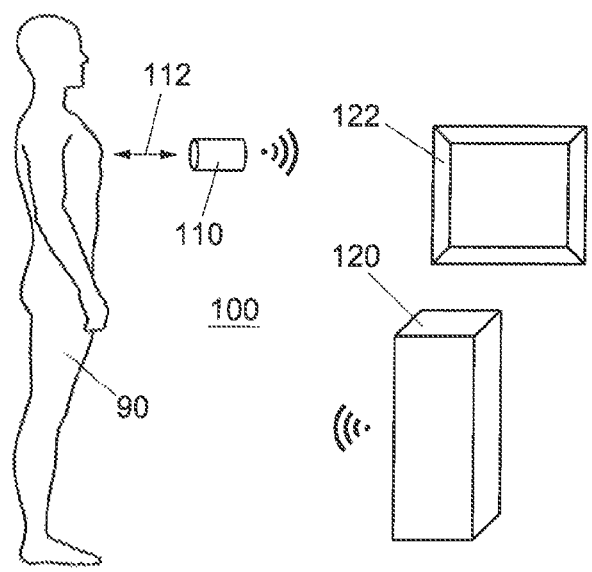
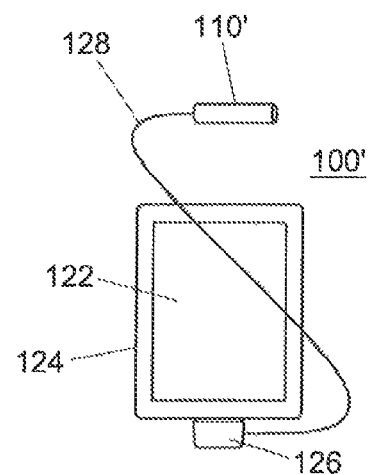
Fig. 2A    Fig. 2B $\omega_1 = 98.4$ bmp; $\omega_2 = 98.4$ bmp $\omega_1 = 112$ bmp; $\omega_2 = 96$ bmp $\omega_1 = 100.8$ bmp; $\omega_2 = 72$ bmp $\omega_1 = 98.4$ bmp; $\omega_2 = 84$ bmp $\omega_1 = 100.8$ bmp; $\omega_2 = 84$ bmp $\omega_1 = 100.8$ bmp; $\omega_2 = 40.8$ bmp $\omega_1 = 136.8$ bmp; $\omega_2 = 69.6$ bmp

| | | |
|---|---|---|
| $\omega_1 >$ | ———▶ | Mild LV dysfunction |
| $\omega_1 >>$ | ———▶ | Severe LV dysfunction |
| $\omega_1 >>>$ | ———▶ | Heart failure |
| $\omega_2 <$ | ———▶ | Middle aged |
| $\omega_2 <<$ | ———▶ | Aging |
| $\omega_2 <<<$ | ———▶ | Aging + Arterial diseases |
| $\Delta\omega >$ | ———▶ | Aging |
| $\Delta\omega >>$ | ———▶ | Arterial or heart diseases |
| $\Delta\omega >>>$ | ———▶ | Arterial and heart diseases |

Fig. 7

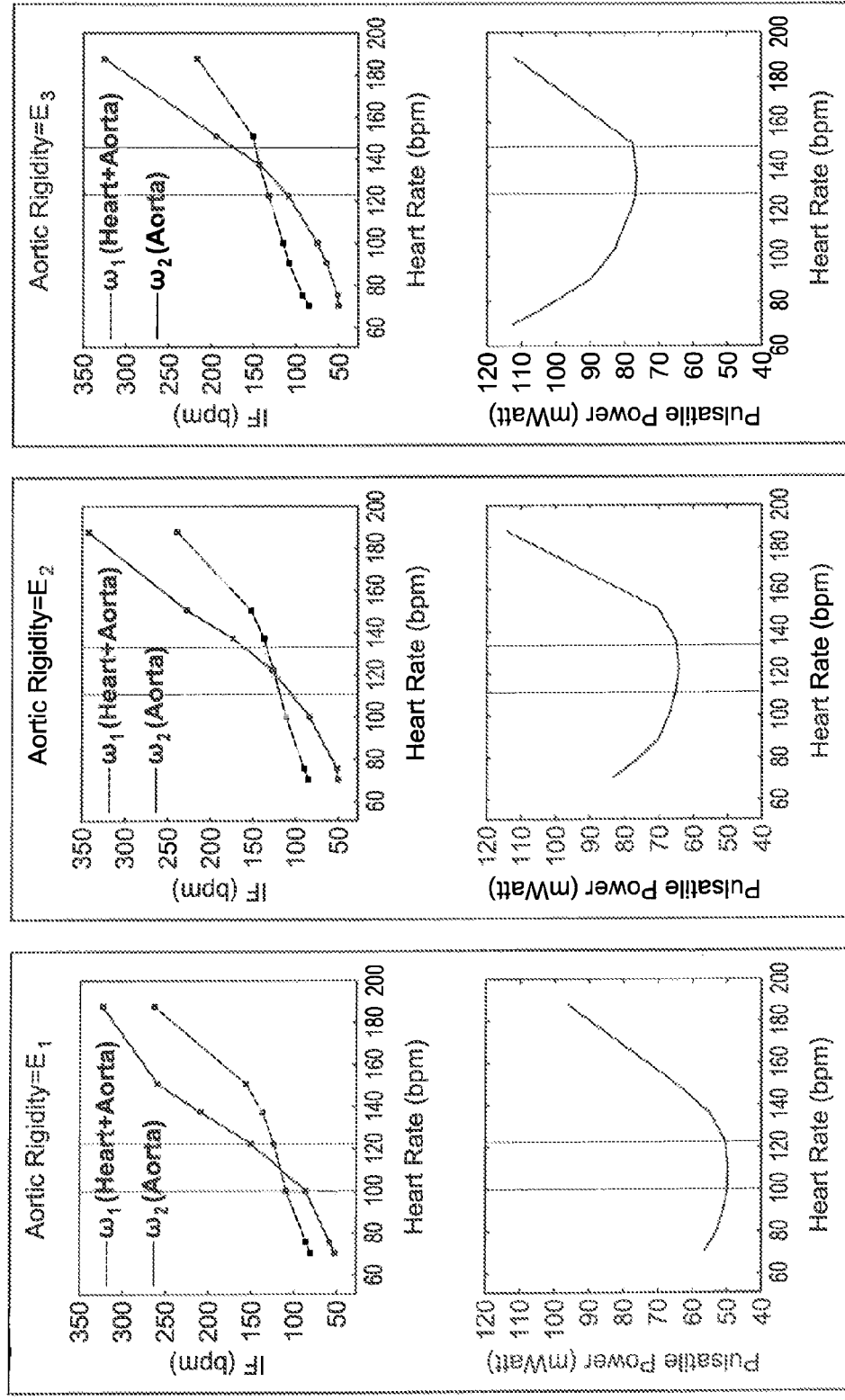

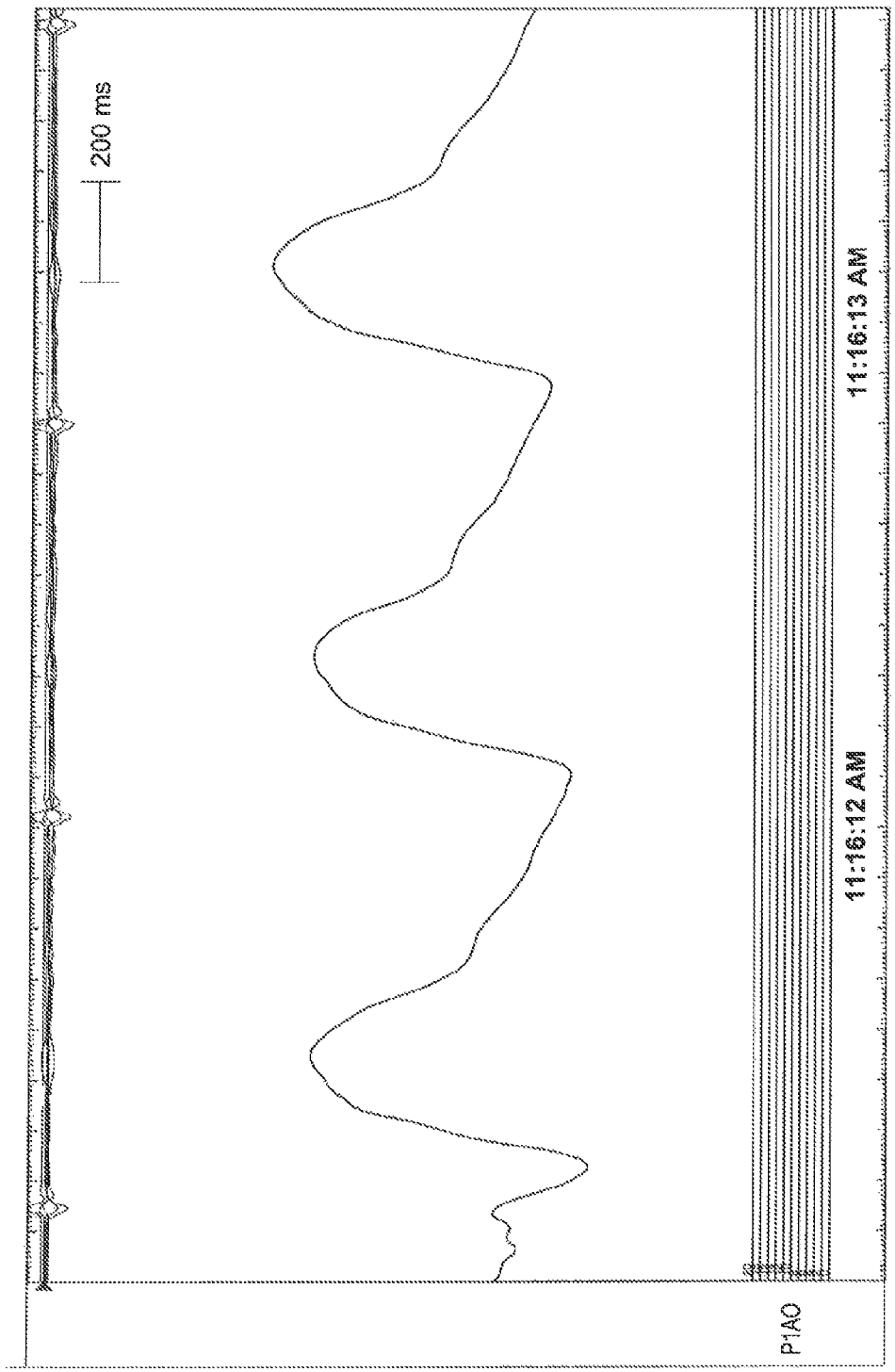

INTRINSIC FREQUENCY HEMODYNAMIC WAVEFORM ANALYSIS

RELATED APPLICATIONS

This filing claims the benefit of U.S. Provisional Patent Application Ser. Nos. 61/579,456 filed Dec. 22, 2011, 61/717,008 filed Oct. 22, 2012 and 61/739,880 filed Dec. 20, 2012, each of which is incorporated by reference herein in its entirety.

FIELD

This filing relates to hemodynamic waveform analysis.

BACKGROUND

Cardiovascular diseases (CVDs) are the underlying cause of about one of every three deaths in United States each year. Likewise, about 34% of American adults are suffering from one or more types of CVD. In 2010, the total direct and indirect cost of CVDs was approximately $503 billion.

Certainly, there is an urgent need to develop new methods and devices for diagnosing and monitoring CVDs. Diagnosis enables early intervention and remediation. Monitoring may be a useful tool in each of behavior modification and prediction/avoidance of an acute event leading to emergency hospitalization, morbidity and/or mortality. New methods and devices to meet these need(s) advantageously employ noninvasive measurements to reduce medical complications and increase patient comfort. Ideally, they are also easy to use by medical personnel and subjects in a home environment.

SUMMARY

The inventive embodiments include devices and systems (e.g., including the sensor hardware referenced herein and the addition of a computer processor and other ancillary/support electronics and various housing elements) and methods (including the hardware and software for carrying out the same) meeting some or all of the aforementioned needs. Such methods and devices are adapted for analysis of the hemodynamic waveform.

This waveform derives from the pulsatile pumping mechanism of the heart. The pumping of blood sends pressure and flow waves into the compliant aorta and vascular network. Pressure and flow waves generated by the heart propagate in the compliant arterial vasculature. These waves get reflected at various reflection sites existing in the arterial system. The intensity and pulsatility of this pressure and resulting dilation wave decreases as the waves enter smaller vessels and eventually disappear in the capillary bed. Therefore, wave dynamics dominate the hemodynamics of large vessels such as the ascending, descending, and abdominal aorta.

These waves carry information about the health or disease state of the heart, vascular system and/or coupling of heart and vasculature. As a result, extracting information from these waves offers the opportunity to make determinations about health or disease conditions that are of great importance.

A healthy heart operates based on a delicate balance between its pumping characteristics (cardiac output, stroke volume) and wave dynamics of the vascular system. This delicate balance can be impaired due to aging, smoking, or disease conditions such as high blood pressure, heart failure, or type-2 diabetes. The analysis devices, systems, and methods herein enable diagnosing, or grading such conditions in terms of severity and/or monitoring a subject's condition.

The subject devices, systems, and methods employ computer analysis of a waveform based on instantaneous/intrinsic frequency theory to provide an index/metric that enables detection of an impaired balance between the heart and aorta at different ages and under various disease conditions. The devices, systems, and methods involve evaluating frequencies of the pressure wave, wall displacement wave or velocity/flow wave (generally: hemodynamic waves) for various detection and monitoring applications. The intrinsic (or dominant) frequencies of a hemodynamic waveform are preferably determined over two or more temporal domains.

At least two of these domains correspond to before and after closing of the aortic valve as apparent in the graph of aortic pressure throughout the cardiac cycle. This graph displays a small dip (the "incisure" or "Dicrotic Notch") in any of the waveforms. Further, devices, systems, methods of detecting the Dicrotic Notch are provided that are useful especially in connection with subjects that suffer valve dysfunction and, thus, limited closure of the valve.

The intrinsic frequencies (also optionally referred to as the dominant frequencies) of the hemodynamic waveform correspond to the frequency that carries the highest energy (or power) among all frequencies in a specific time interval of the instantaneous frequency. The subject devices, systems and methods include means for directly calculating these values. They also include means of estimating the dominant frequencies (intrinsic frequencies) as elaborated upon below.

However determined in the embodiments hereof, only the shape of the hemodynamic waves (an uncalibrated waveform) are needed for determining the intrinsic/dominant frequencies for each part of the waveform. Magnitude of the hemodynamic wave(s) is not required. As such, noninvasive hardware and methodology such as ultrasound, echocardiography and cardiac microwave can be used for measurements. Moreover, a need for measurement system calibration is avoided. Thus, tonomeric type sensor hardware is also easily employed as are optical and other sensor devices—any of which type scanner may be used to provide a hemodynamic waveform input signal for the subject devices, systems, and methods.

However, the hardware is configured, in an acute setting (whether with a primary care physician or a specialist) systems running software according to the subject methodology may be used to detect atrial fibrillation or aortic valve dysfunction and the need for surgical intervention. Alternatively, such devices may be employed for monitoring (daily at home or periodically with a primary care physician) as part of long-term care in connection with medicating for hypertension or monitoring congestive heart failure (CHF). By observing changes in hemodynamic waveform status, the embodiments may also be useful for predicting the type of events leading to or requiring hospitalization.

Moreover, variations of the devices, systems, and methods herein, where intrinsic frequency of a given waveform is determined, enables a range of other applications. These include diagnosing diastolic dysfunction, atrial fibrillation, low cardiac output, aortic insufficiency or approximating stroke volume, the risk of coronary artery disease, prediction of restenosis after coronary stent placement (all through the pressure or vessel wall displacement waveform) or diagnosing mitral regurgitation through the velocity waveform.

BRIEF DESCRIPTION OF THE DRAWINGS

The figures provided herein illustrate examples and embodiments and may be diagrammatic and not necessarily drawn to scale, with some components and features exaggerated and/or abstracted for clarity. Variations from the embodiments pictured are contemplated. Accordingly, depiction of aspects and elements in the figures are not intended to limit the scope of the claims, except when such intent is explicitly stated.

FIGS. 1A and 1B diagrammatically illustrate the dynamic coupling of the heart and aorta in a human circulatory system.

FIGS. 2A and 2B illustrate example embodiments of the systems described herein.

FIG. 7 is a table presenting possible diagnoses associated with the subject IF values.

FIGS. 12A-12C and 13A-13C are panels illustrating the hemodynamic analysis of quantified models.

FIGS. 14A-14C illustrate the pressure waveform of three blind test examples.

DETAILED DESCRIPTION

Figure 3A:
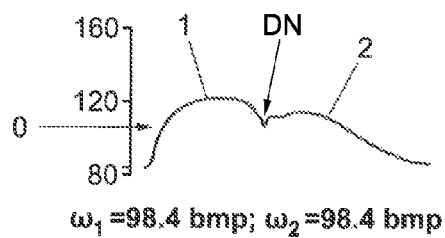
FIGS. 3A and 3B illustrate the pressure waveforms of two young adults and their calculated IF values.

Various example embodiments are described below. Reference is made to these examples in a non-limiting sense. They are provided to illustrate more broadly applicable aspects of inventive aspects. Various changes may be made to the embodiments described and equivalents may be substituted without departing from their true spirit and scope. In addition, many modifications may be made to adapt a particular situation, material, composition of matter, process, process act(s) or step(s) to the objective(s), spirit or scope of the claims made herein.

That said, the present subject matter is based on the fact that a healthy heart-aorta system in the human body represents a delicate coupling between heart pumping characteristics and aortic (arterial) wave dynamics. This optimum coupling becomes impaired by arterial diseases (e.g., arterial stiffening, aging, hypertension), heart diseases (e.g., heart failure, coronary diseases) or other negative contributors (e.g., smoking).

FIG. 1A illustrates a coupled heart-aorta system 10 in systole, with the aortic valve open (not shown) and blood being pumped by the heart 12 into the aorta 14. As such, the heart and aorta construct a coupled dynamic system before the closure of the aortic valve. As shown in FIG. 1B, after the valve closure during diastole, the heart and aortic systems are decoupled in a second system state 10'. The aortic waves contain in each state include information about heart dynamics, arterial network dynamic and heart-aorta coupling.

Extraction of such information by analysis as described in further detail herein is based on intrinsic (instantaneous) frequency and includes devices, systems, and methods for:

diagnosis of different CVDs from a pressure waveform;

evaluation of the severity of CVD from a pressure waveform;

diagnosis of different CVD from a wall displacement waveform;

evaluation of the severity of CVD from a wall displacement waveform;

diagnosis of different CVDs from a flow waveform;

evaluation of the severity of CVD from a flow waveform;

diagnosis of different CVDs from a combination of pressure, wall displacement, and/or flow waveform; and evaluation of the severity of CVD form combination of pressure, wall displacement and/or flow waveform.

Traditional methods of data analysis are based on the assumption of data being stationary and linear. Fourier analysis is just a typical, and often used, method. However, it is a known fact that the stationarity and linearity assumptions do not hold for arterial waves. Yet, a new method of Sparse Time-Frequency Representation (STFR) has been developed that may be applied herein to achieve the above, and still other methods and goals.

The STFR method is employed because it is well suited for nonlinear data analysis, it is less sensitive to noise perturbation and, more importantly, it preserves some intrinsic physical property of the signal. The general STFR problem is defined as follows:

$$\text{Minimize } M \quad (1)$$
$$\text{Subject to: } s(t) = \sum_{i=1}^{M} a_i(t)\cos\theta_i(t), \ a_i(t)\cos\theta_i(t) \in D$$
$$i = 1, \dots, M$$

In the subject devices, systems, and methods, a simplified and modified version of STFR may be employed by minimizing:

$$\|f(t) - a_1 X(0, T_0)\cos\omega_1 t - b_1 X(0, T_0)\sin\omega_1 t - \quad (2)$$
$$a_2 X(T_0, T)\cos\omega_2 t - b_2 X(T_0, T)\sin\omega_2 t - c\|_2^2$$
$$X(a, b) = \begin{cases} 1 & a \le t \le b \\ 0 & \text{otherwise} \end{cases}$$

Subject to:
$$\begin{cases} a_1 \cos\omega_1 T_0 + b_1 \sin\omega_1 T_0 = a_2 \cos\omega_2 T_0 + b_2 \sin\omega_2 T_0 \\ a_1 = a_2 \cos\omega_2 T + b_2 \sin\omega_2 T \end{cases}$$

where, $T_0$ is the time of aortic valve closure (i.e., the charted Dicrotic Notch) in order to determine intrinsic/dominant frequency (IF) values ($\omega_1$, $\omega_2$) in the two domains on either side of the Dicrotic Notch.

Still, it is to be recognized that the IF values can be approximated and still fall within the spirit and scope of the subject embodiments. In one example, the IF values are approximated using the graph of the instantaneous frequency ($\dot{\theta}_1(t)$) of method of equation (1). Possible indices that can be used to approximate $\omega_1$ and $\omega_2$ as such include:

$\overline{\omega_1}$ approximating $\omega_1$ by averaging the $\dot{\theta}_1(t)$ over an specific time period before the $\dot{\theta}_1(t)$ transition (when the aortic valve is open);

$\overline{\omega_2}$ approximating $\omega_2$ by averaging the $\dot{\theta}_1(t)$ over an specific time period after the $\dot{\theta}_1(t)$ transition (when the aortic valve is closed);

$\overline{\omega_1}$ approximating $\omega_1$ by averaging the maximum and minimum value of $\dot{\theta}_1(t)$ curve before the $\dot{\theta}_1(t)$ transition (when the aortic valve is open);

$\overline{\omega_2}$ approximating $\omega_2$ by averaging the maximum and minimum value of $\dot{\theta}_1(t)$ curve after the $\dot{\theta}_1(t)$ transition (when the aortic valve is closed);

$\omega_1^{max}$ approximating $\omega_1$ using the one of the local maximum of $\dot{\theta}_1(t)$ curve before the $\dot{\theta}_1(t)$ transition (when the aortic valve is open);

$\omega_1^{min}$ approximating $\omega_1$ using the one of the local minimum of $\dot{\theta}_1(t)$ curve before the $\dot{\theta}_1(t)$ transition (when the aortic valve is open);

$\omega_2^{max}$ approximating $\omega_1$ using the one of the local maximum of $\dot{\theta}_1(t)$ curve after the $\dot{\theta}_1(t)$ transition (when the aortic valve is closed); and $\omega_2^{min}$ approximating $\omega_1$ using the one of the local minimum of $\dot{\theta}_1(t)$ curve after the $\dot{\theta}_1(t)$ transition (when the aortic valve is closed).

Likewise, it is possible to calculate or approximate IF by other known time-frequency analyses such as Empirical Mode Decomposition (EMD) methods (see U.S. Pat. No. 6,738,734 to Huang, incorporated herein by reference in its entirety) and Wavelet methods.

As evident, any/all such calculation either for directly calculating IF values or approximating them requires the use of a computer processor. As discussed further below, FIGS. 3A-5B illustrate pressure waveforms for which $\omega_1$, $\omega_2$ IF values have been calculated. These calculations took computer-scanned values from printed published pressure waveform data and processed such data with a general purpose computer processor.

FIGS. 2A and 2B illustrate example systems that are capable of acquiring such waveform information and/or processing the same. The IF results based on the same may be produced and/or displayed in real time for physician evaluation and/or logged for monitoring or subsequent evaluation of a physician or other analysis. Alternatively, diagnosis based on the IF results may be displayed, alarms triggered, etc. for users who are not either medically or specially trained (e.g., as in the case of home use or general practice physicians.) Regardless, what is meant by "real time" in the context above will generally mean that it takes about 1 second or less from the time of data acquisition for calculation and data presentation, more often such action is essentially without delay. In any case, real time activity in the subject embodiments concerns manipulation of such a mass of data and calculations that the task is well beyond practicable human capacity, thereby requiring the use of a computer processor.

In any case, FIG. 2A diagrammatically illustrates a computer-based system 100 in which a scanner 110 includes on-board electronics for sending and receiving signals 112 to acquire hemodynamic waveform measurements. Use of a microwave sensor (at least for measuring vessel displacement) and/or ultrasound sensors (for measuring either or both vessel distension and blood velocity/flow) for such purposes is well known. An example of suitable publicly-available hardware includes that employed in the GE LOGIQ Book Portable Ultrasound Machine, which technology is readily adapted to the subject devices, systems, and methods. Suitable microwave sensor technology is described in Fletcher, R R, and S Kulkarni, "Clip-on wireless wearable microwave sensor for ambulatory cardiac monitoring," IEEE, 2010. 365-369. Web. 3 Feb. 2012.

Other types of scanners may be used as well. These include tonomeric and optical units. In the former case, the tonomeric sensor will include a force or pressure sensing transducer producing an electronic signal corresponding to a pressure or wall-displacement based hemodynamic waveform. The optical scanner may embody any of a variety of technologies in producing a signal that correlates to a hemodynamic waveform. In one embodiment, the optical scanner may include infrared (IR) diode(s) and sensor(s) suitable for measuring a wall displacement waveform. In another embodiment, the scanner operates as a camera. In which case (whether in a flat-bed scanner format, in typical stand-alone digital camera format, or incorporated in the bezel of a iPAD or the like), such a device is able to capture a printed or otherwise displayed hemodynamic waveform and convert it to a digital representation employing a CCD, CMOS or the like. Then, a computer program such as the UN-SCAN-IT Graph Digitizer can be employed to produce a signal representative of the captured hemodynamic waveform to be received by a computer processor for analysis.

Scanner 110 may be hand-held for scanning a seated or standing patient 90 as shown. Or the scanner hardware may be incorporated in a C-arm or tunnel for scanning a patient lying down.

A hand-held scanner may advantageously be battery-powered so as to avoid connection to a wall socket. Whether hand-held or incorporated or in a larger unity, scanner 110 may interface by wireless (as indicated) or wired (not shown) communication with a general purpose computer 120, optionally including display 122 to perform and communicate results, respectively. Otherwise, on-board processing and/or display hardware may be provided in connection with the sensor housing itself. Such options may be especially useful for a hand-held or semi-portable device as these may be used by a patient/subject at home, during travel, etc.

Notably, all the hardware may be located in one location. Alternatively, the computer system may be located at a remote location as in a "Cloud" based option. Further, the system may consist of the computer and its programming without a sensor means. In which case, the system may include an optical scanner or other camera means for image or other electronic capture of a waveform produced by another (already available) measurement machine (e.g., the aforementioned GE scanner, etc.).

As yet another option, FIG. 2B, illustrates a portable system 100'. It includes a tablet-style computer device 124 (e.g., an iPAD) with an integral display 122. A tonomeric or optical scanner sensor probe 110' is shown connected to computer 124 via a bus 126 and wired connection 128. However, the scanner (of whatever type) may be wirelessly connected as in the previous example as well. Alternatively, the scanner employed in capturing the hemodynamic waveform may be the camera 110" integrated in the device.

Regardless of how the hemodynamic waveforms are acquired, a given waveform 0 is analyzed in the subject method to produce two IF values. Per FIG. 3A, these correspond (exactly or approximately) to $\omega1$ and $\omega2$ for a first section/domain 1 in which the heart and aorta are in a coupled system 10 and a second section/domain 2 for the aorta in a system 10' alone. These domains are separated/delineated by the Dicrotic Notch (DN) as shown.

FIG. 3A also shows a scale for the pressure measure of the waveform. However, as commented upon, the scale of the waveform is not important—merely its shape. More notable are the $\omega1$ and $\omega2$ values determined from FIGS. 3A-5B.

Figure 3B:
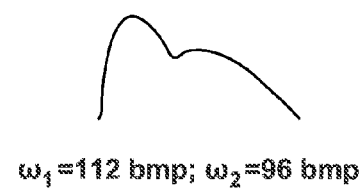

Accordingly, FIGS. 3A and 3B illustrate the pressure waveforms of two young adults and their calculated IF values.

Figure 4A:
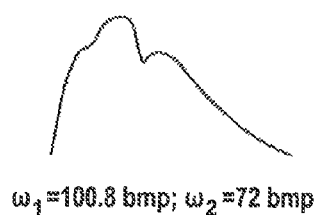
FIGS. 4A-4C illustrate the pressure waveforms of three 30-40 year old adults and their calculated IF values.
Figure 4B:
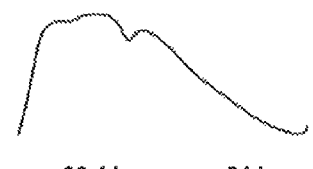
Figure 4C:
Figure 5A:
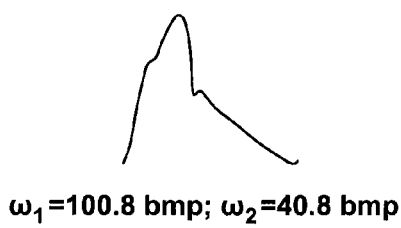
FIGS. 5A and 5B illustrate the pressure waveforms of an aged adult and another with severe heart failure, respectively, with their calculated IF values.
Figure 5B:

The data are from young healthy adults when heart+aorta system and arterial wave dynamics are on their optimum condition (or close to optimum). The IF values are close to each other. FIGS. 4A-4C illustrate the pressure waveforms of three 30-40 year old adults and their calculated IF values. The data are from adults when heart+aorta system and arterial wave dynamics are getting off of their optimum condition, likely due to increased aortic rigidity. In these examples, the IF values are further separated than those from FIGS. 3A and 3B. FIGS. 5A and 5B illustrate the pressure waveforms of an aged adult and another with severe heart failure, respectively, with their calculated IF values. The difference between the IF values is considerably larger.

Figure 6A:
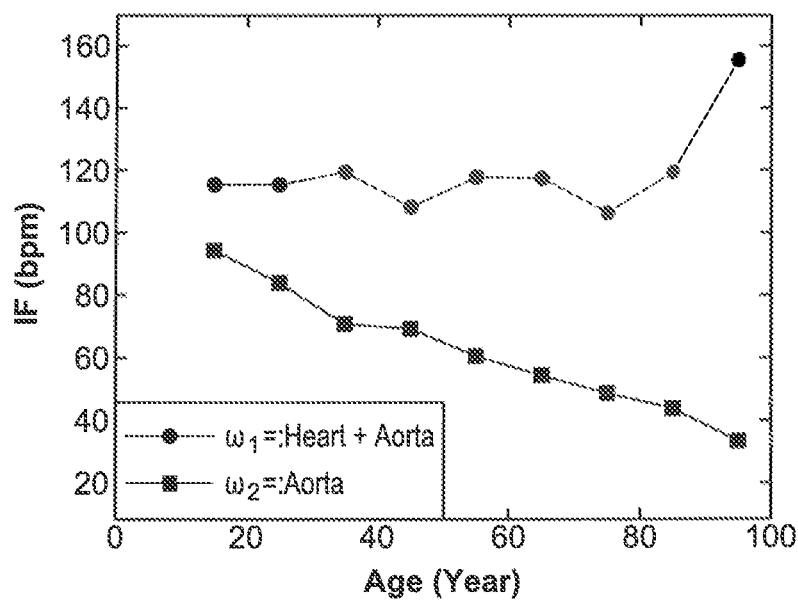
FIG. 6A plots trends in hemodynamic waveform IF.
Figure 6B:
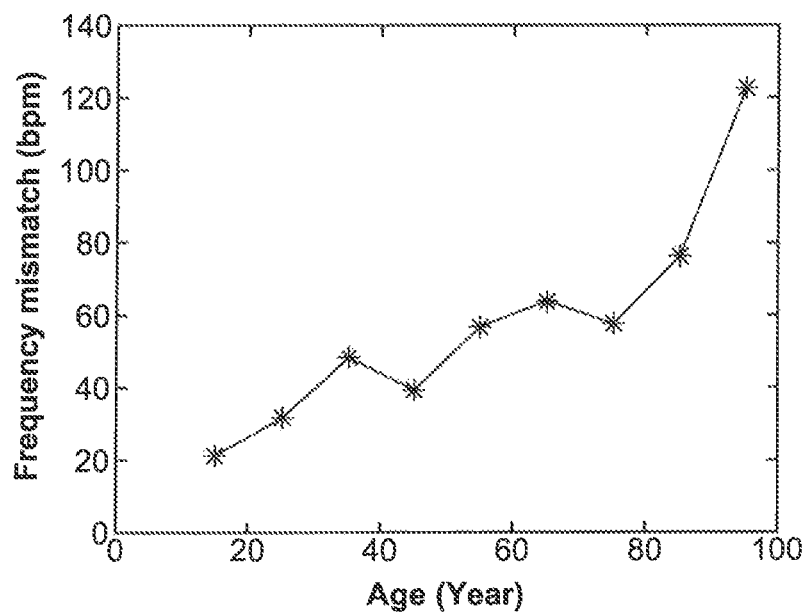
FIG. 6B plots the difference in the FIG. 6A IF values.

FIG. 6A illustrates plotted trends in calculated IF for the first and second waveform domains. Even with the limited data set, it is clear that $\omega 1$ either stays relatively constant or increases with age while $\omega 2$ decreases with age. Thus, in the plot of FIG. 6B showing difference between IF values, the difference increases with age.

Similarly, based on the observation of known conditions for a variety of subjects and their associated IF waveform values, it is possible to develop a database and propose correlations between the IF values and cardiac health/CVD conditions. Such an effort is represented in the table of FIG. 7. Here, relative ($>$ or $<$) $\omega 1$, $\omega 2$ and $\Delta\omega$ values are tabulated as indicative of various possible conditions. Backed by appropriate study power, such a table may be provided as an aid to physicians interpreting IF analysis output from a system 100/100'. Alternatively, the relations/logic for the table may be embedded in programming such a system to offer diagnosis independent of physician feedback/interpretation.

Figure 8:
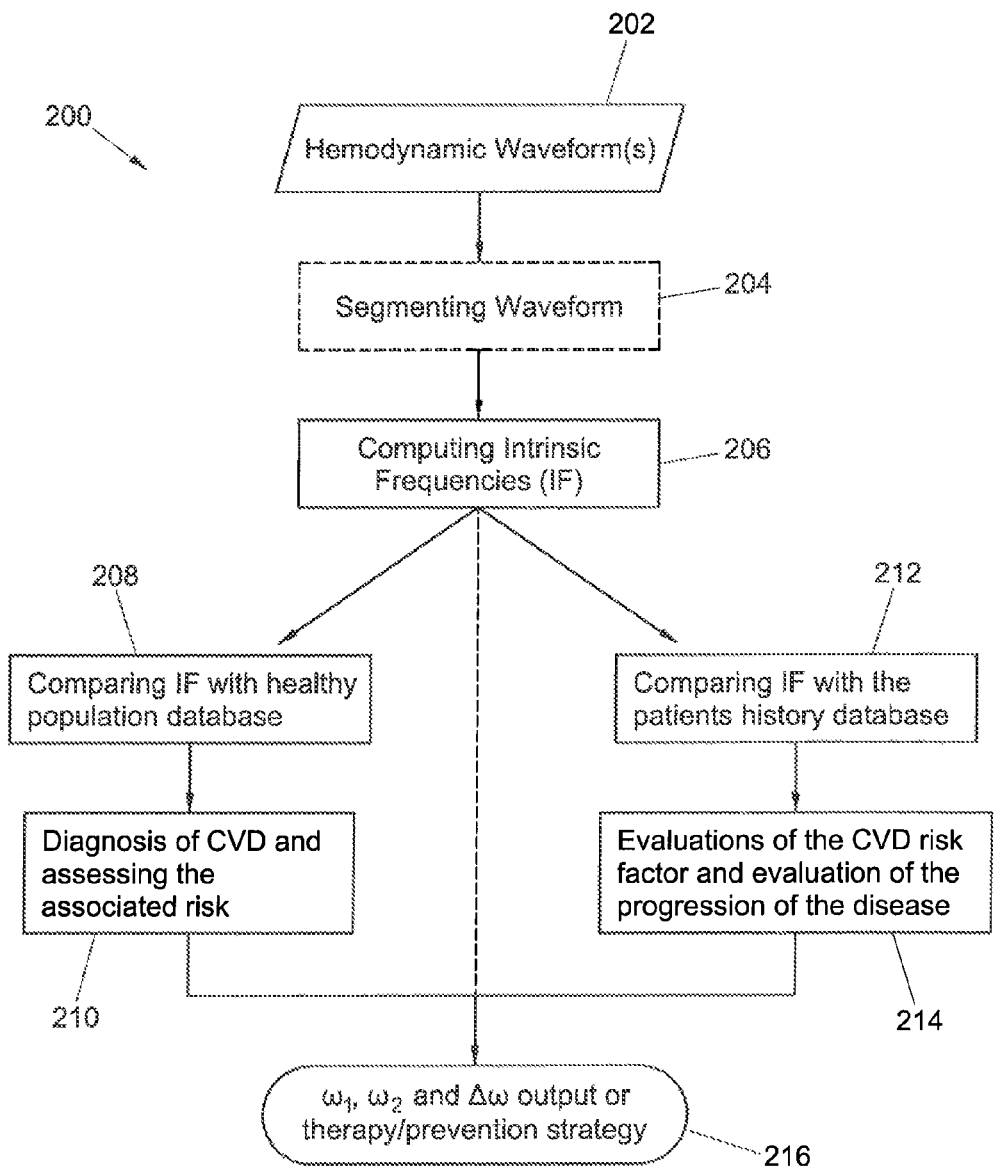
FIG. 8 is a process flowchart illustrating various method options hereof.

In any case, FIG. 8 is an example of a computer program flowchart 200 illustrating general and specific processes that may be carried out according to the subject methods. At 202 hemodynamic waveform data is acquired and/or input in electronic format. At 204 the waveform date is optionally segmented at the position of the Dicrotic Notch. This may be a process as discussed further below, or inherent to 206 where IF values are calculated. The computer process may then terminate with the output (by graphic display, printout, etc.) of $\omega 1$, $\omega 2$ and $\Delta\omega$ for physician evaluation. Otherwise the computer program at 208 may interrogate and compare the IF values with a database of values characteristic of health; based on this comparison, at 210 the program can offer a diagnosis of CVD and assess the associated risk. Alternatively or additionally, at 212 the process may proceed to compare the current IF values with a database containing historical IF values for the patient, with subsequent evaluation of CVD risk factor and/or disease progression determination at 214. Following any such evaluation, at 216 the program may suggest associated therapy, preventive stratagem or the like—including prompting immediate hospitalization if the onset of a cardiac event is detected.

Figure 9A:
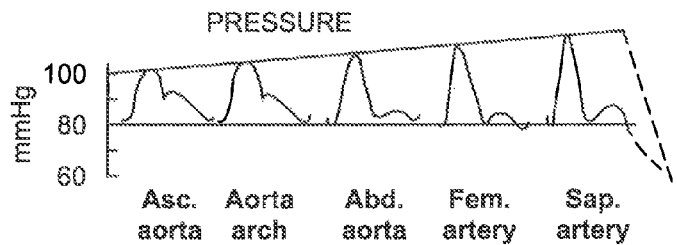
FIGS. 9A and 9B illustrate the characteristic change in contours in pressure wave and flow wave between the ascending aorta and the saphenous artery, respectively.
Figure 9B:
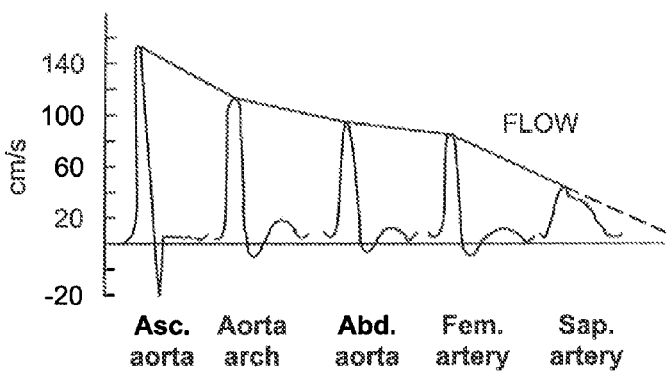

Regarding the input or acquired waveform, it may be taken at any of a selected arterial site. FIGS. 9A and 9B illustrate the characteristic change in contours in pressure wave and flow wave between the ascending aorta and the saphenous artery, respectively. Either type of wave at any of the locations may be employed. However, it may sometimes be advantageous to take the measurements close to the location associated with the corresponding disease (e.g., close to the heart for heart diseases)

Figure 10A:
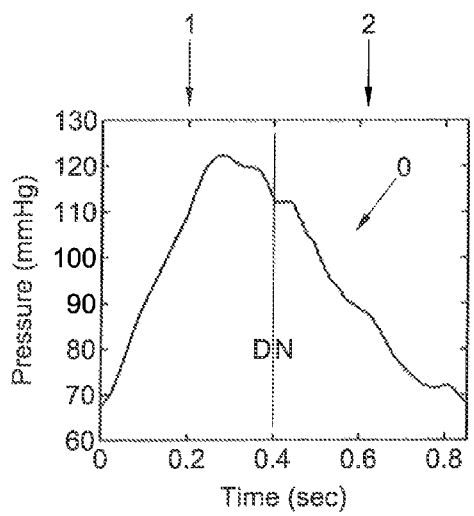
FIG. 10A is an example of a modeled pressure waveform.
Figure 10B:
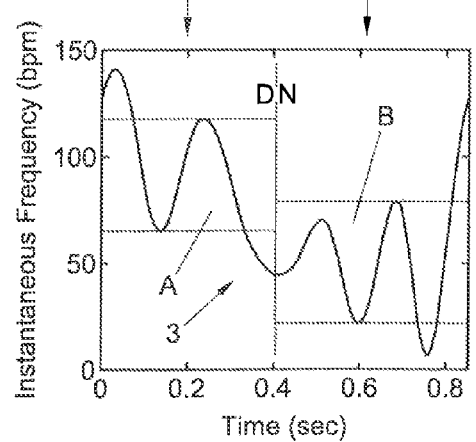
FIG. 10B illustrates instantaneous waveform frequency associated therewith.

FIG. 10A is an example of a pressure waveform from a computational model of the aorta. The computational model was physiologically relevant. The methods, as well as the physical parameters of the model, are described in Pahlevan N M, Gharib M. "Aortic wave dynamics and its influence on left ventricular workload," PLoS ONE. 2011; 6:e23106 incorporated herein by reference in its entirety and discussed further below. Relevant to the present discussion, however, FIG. 10B illustrates the calculated instantaneous waveform frequency 3 from the waveform of FIG. 10A. Notably, the instantaneous frequency in each of domain 1 and 2 is oscillating around certain dominant frequencies in two range bands A and B. The system IF values fall within these bands. As noted above, the IF values can be calculated or estimated within these bands.

Figure 11A:
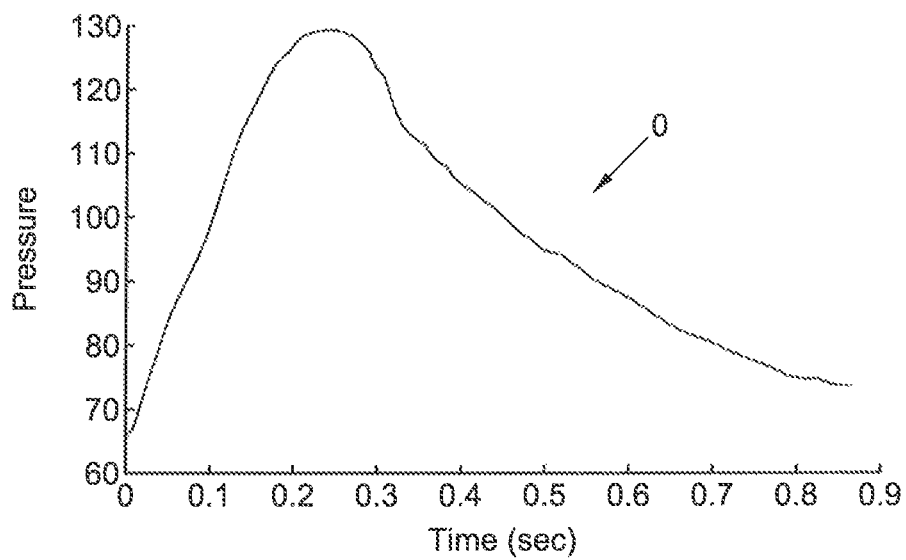
FIG. 11A is an example of a pressure waveform of a subject whose dicrotic notch is not easily distinguishable from the pressure waveform.
Figure 11B:
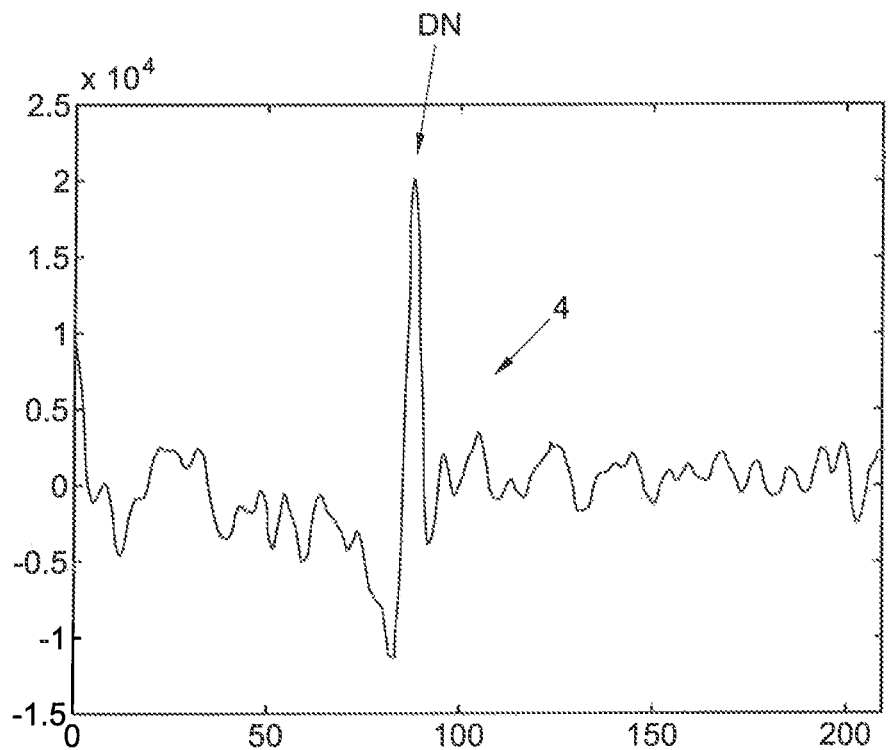
FIG. 11B illustrates the second derivative of the waveform.
Figures 12A, 12B, 12C:
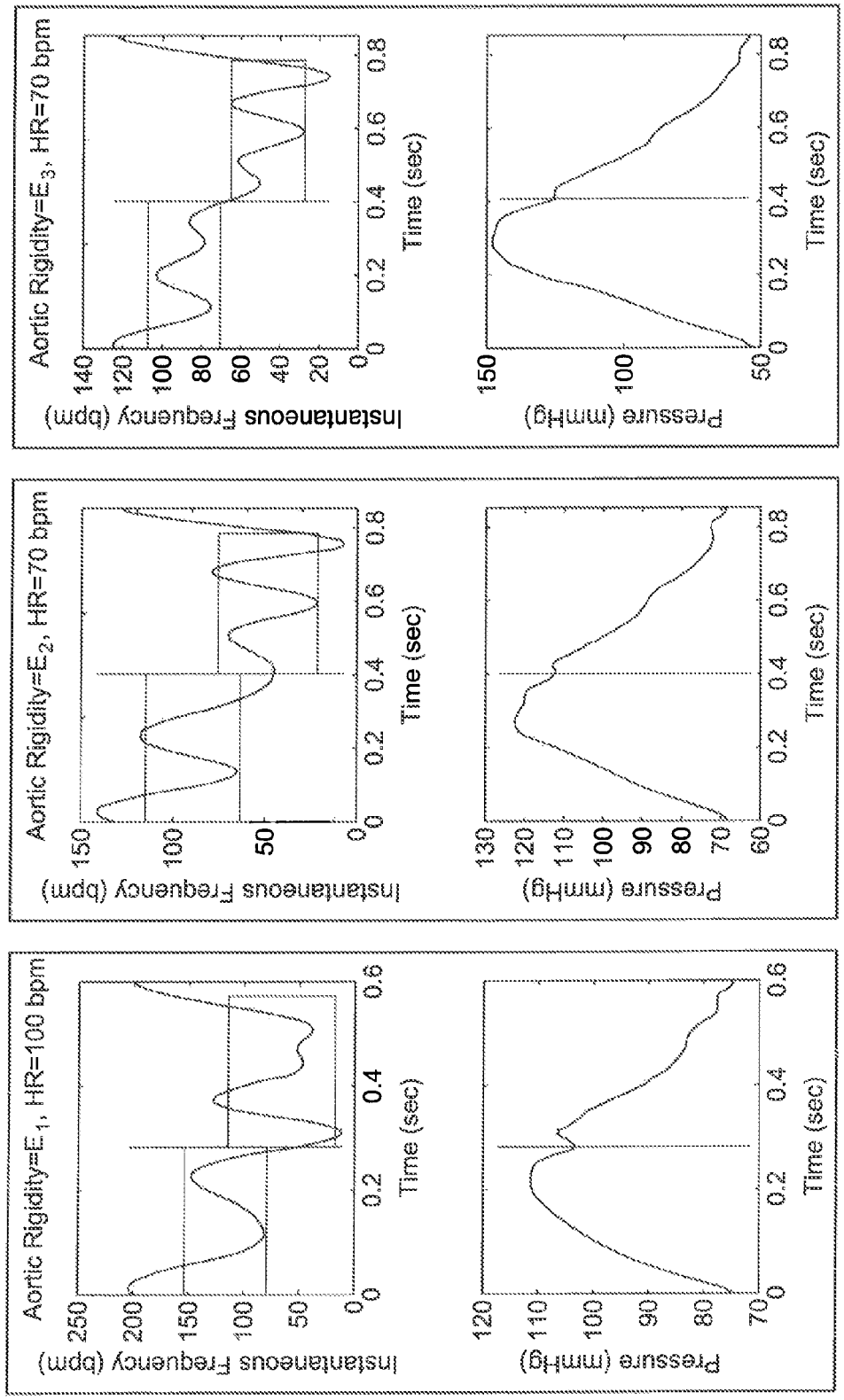

Moreover, as alluded to above, the shape of the instantaneous frequency waveform may be employed to determine the position of the Dicrotic Notch (DN) where the waveform changes the oscillation range as shown. Another approach to identifying the Dicrotic Notch is presented in connection with FIGS. 11A and 11B. In FIG. 11A, a waveform 0 is provided for a subject whose dicrotic notch is not easily distinguishable from pressure waves (patients with severe valve diseases usually fall in this category). Thus there is very little noticeable indication of aortic valve closure. However, a second derivative plotting 4 of the original waveform 0 yields a sharp peak indicative of the Dicrotic Notch. Finding DN by either approach may constitute a sub-process within flowchart element 204.

EXAMPLES

Various additional examples are provided herein. A first set of examples is presented in connection with FIGS. 12A-12C and 13A-13C, which relate the underpinnings of the subject IF values. The second set of examples presented in connection with FIGS. 14A-14C were the subject of a blind study where diagnosis was attempted for patients that had otherwise been physician-tested.

Model Examples

Regarding the first examples, these represent work with a computational model of the aorta. Full details of the computational model are as cited above. So-configured, simulations were performed for different levels of aortic rigidities labeled $E_1$ through $E_7$, where $E_1$ is the aortic rigidity of a 30-year old healthy individual. All the other $E_i$ are multiplicative factor of $E_1$ as: $E_2=1.25E_1$, $E_3=1.5E_1$, $E_4=1.75E_1$, $E_5=2E_1$, $E_6=2.5E_1$, and $E_7=3E_1$. At each $E_i$, simulations were completed, providing computed pressure waveforms for eight heart rates (70.5, 75, 89.5, 100, 120, 136.4, 150, and 187.5 beats per minute (bpm)). The pressure waveforms for $E_1$-$E_3$ at 100, 70 and 70 bpm are shown in FIGS. 13A-13C, respectively. Intrinsic frequencies, were also computed using equation (2) with results as shown.

As discussed above, IF values can be estimated from the instantaneous frequency or can be calculated. Here, in this example they were calculated for each rigidity at each pulse (bpm) rate. The results of such are presented for E1-E3 in FIGS. 13A-13C.

Also discussed above, is the hypothesis based on data obtained from young, healthy individuals that optimal heart coupling is present (as indicative of optimal health) when the IF values (i.e., $\omega 1$ and $\omega 2$) are equivalent. If true, the intersection of the $\omega 1$ and $\omega 2$ plots in FIGS. 13A-13B should yield and be equivalent to the optimal heart rate. This range is represented in the vertical band across each graph.

Most interesting, is that the results of this hypothesis exactly match the results of another presented in connection with the model arrived at from another perspective. Namely, in Pahlevan, et al., optimal heart rate for the model was argued to be when left ventricular (LV) pulsatile load is minimized. The computationally determined minimum pulsitile power also shown in FIGS. 13A-13B occur at the same rate as predicted by the $\omega_1$-$\omega_2$ intersection. As such, additional corroboration is offered for the use of IF as an indicator of cardiovascular health (with respect to a stated optimal condition of zero difference between $\omega_1$ and $\omega_2$).

Blind Test Examples

Figure 14B:
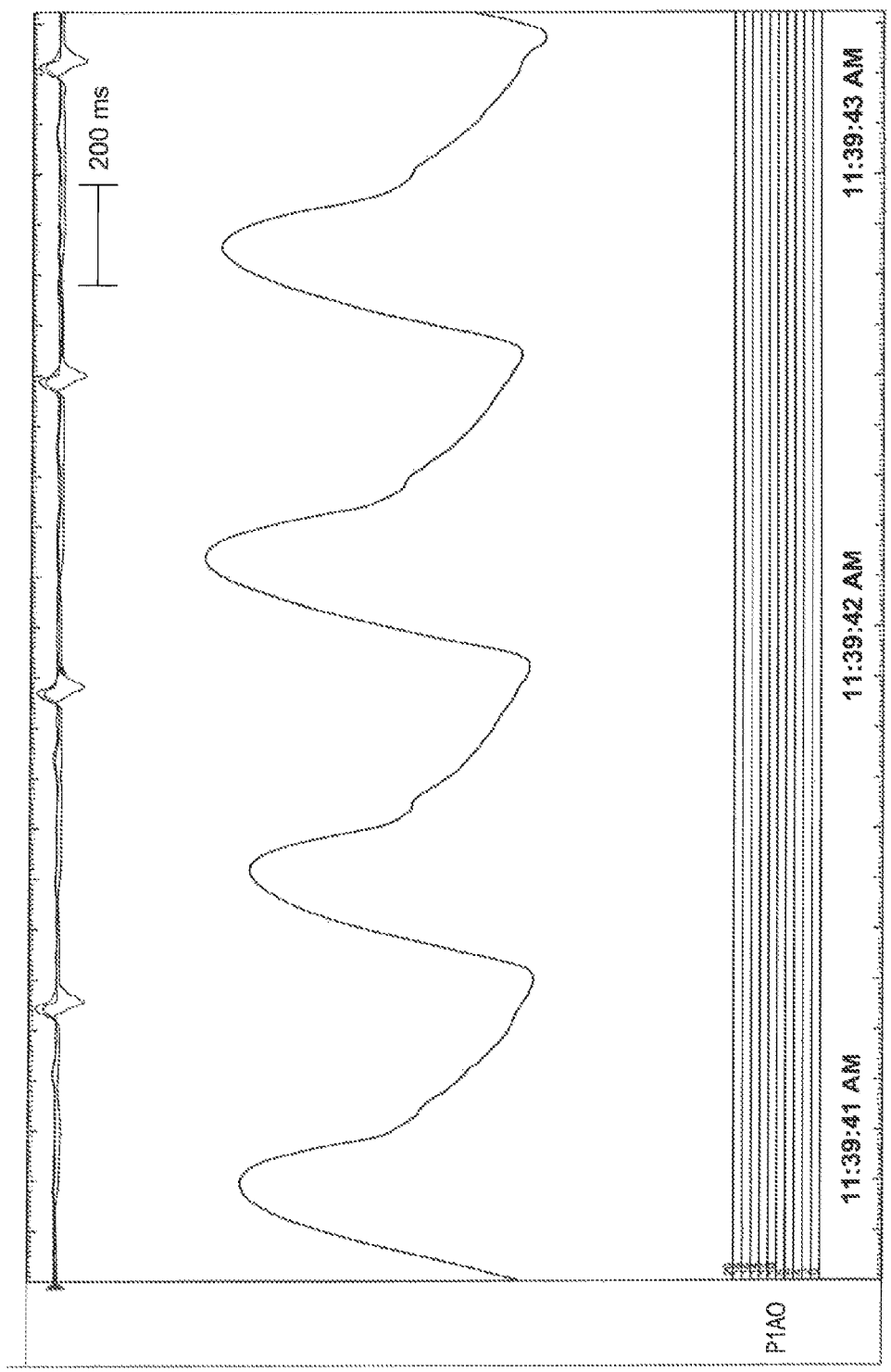
Figure 14C:
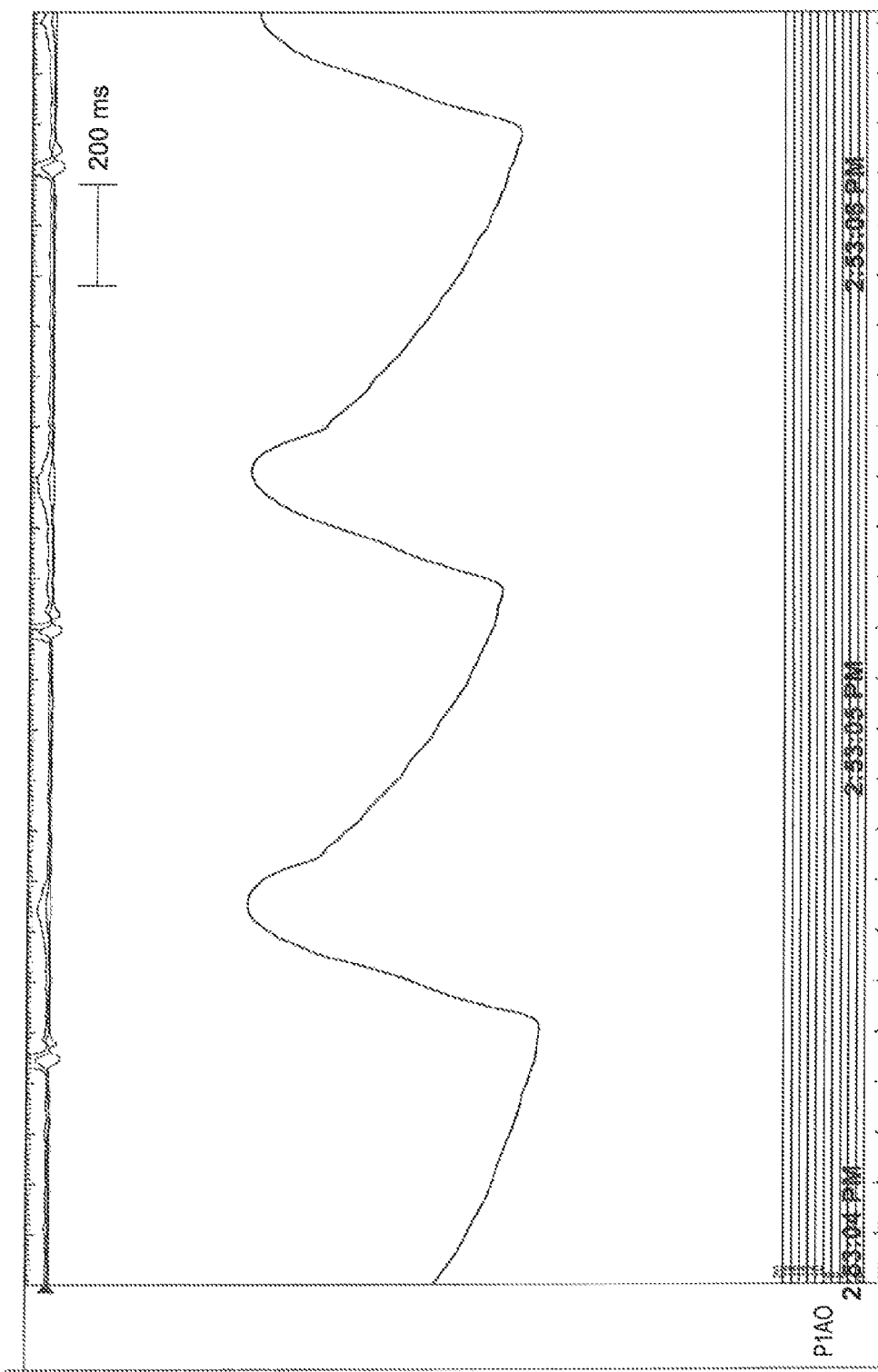

Further corroboration of the value of IF as a predictive value of cardiac health is presented in connection with FIGS. 14A-14C. Recorded pressure waveforms were provided and scanned/digitized. The subject STFR method was then applied to each and a diagnosis by the inventors hereof of the possible health condition of the patent was made without consulting the physician who provided the data and made an independent diagnosis without the use of IF values. As evident from the below, the IF-predicted health status offered good agreement with the patient status.

For the waveform presented in FIG. 14A, with a HR of 79.4 with calculated $\omega_1$=73.2, $\omega_2$=52.3 and $\Delta\omega$=20.9, the following observations were made:

$\omega_1$ was less than HR indicating LV dysfunction (severe abnormality);

$\omega_2$ was low indicative indicating mild arterial rigidity (consistent with 35-45 year old male or 55-65 year old female); and $\Delta\omega$ was low indicating good heart-aorta coupling In fact, the patient was a 66-year-old female with no history of hypertension, she had a normal ejection fraction, but presented with atypical chest pain of indeterminate cause.

For the waveform presented in FIG. 14A, with a HR of 97.5 with calculated $\omega_1$=121.4, $\omega_2$=44 and $\Delta\omega$=77.4 the following observations were made:

$\omega_1$ was high indicating LV dysfunction;

$\omega_2$ was very low indicating severe arterial rigidity (consistent with 60+ year-old male); and $\Delta\omega$ was very high indicating severe out-of-optimum coupling (indicative of severe arterial rigidity and heart diseases). In fact, the patient was a 65-year-old male with severe coronary disease; he had very poor LV function with an ejection fraction of 25%.

For the waveform presented in FIG. 14A, with a HR of 69.5 with calculated $\omega_1$=113, $\omega_2$=31.4 and $\Delta\omega$=81.6 the following observations were made:

$\omega 1$ was not particularly high indicating no severe LV dysfunction;

$\omega 2$ was extremely low indicating aging and arterial disease (consistent with a 60+ year-old male); and $\Delta\omega$ was very high indicating severe out of optimum coupling (consistent with arterial and heart diseases).

In fact, the patient was a 71-year-old male with coronary disease, atrial fibrillation and a history of hypertension.

Variations

In addition to the embodiments that been disclosed in detail above, still more are possible within the classes described, and the inventors intend these to be encompassed within this specification and claims. This disclosure is intended to be exemplary, and the claims are intended to cover any modification or alternative which might be predictable to a person having ordinary skill in the art.

Moreover, the various illustrative processes described in connection with the embodiments herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has a user interface port that communicates with a user interface, and which receives commands entered by a user, has at least one memory (e.g., hard drive or other comparable storage, and random access memory) that stores electronic information, including a program that operates under control of the processor and with communication via the user interface port, and a video output that produces its output via any kind of video output format, e.g., VGA, DVI, HDMI, DisplayPort, or any other form.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein. The camera may be a digital camera of any type including those using CMOS, CCD or other digital image capture technology.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software, the functions may be stored on, transmitted over or resulting in analysis/calculation data output as one or more instructions, code or other information on a computer-readable medium. Computer-readable media includes both computer storage media and communication media, including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

Operations as described herein can be carried out on or over a website. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

Also, the inventors intend that only those claims which use the words "means for" are intended to be interpreted under 35 USC 112, sixth paragraph. Moreover, no limitations from the specification are intended to be read into any claims, unless those limitations are expressly included in the claims. The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, it is contemplated that any optional feature of the embodiment variations described may be set forth and claimed independently, or in combination with any one or more of the features described herein. Reference to a singular item, includes the possibility that there is a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as in the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of the claim language. All references cited are incorporated by reference in their entirety. Although the foregoing embodiments been described in detail for purposes of clarity of understanding, it is contemplated that certain modifications may be practiced within the scope of the appended claims.

Accordingly, we claim:

1. A system for acquiring and analyzing a hemodynamic waveform of a subject, the system comprising:
    an optical scanner, the scanner adapted to capture a signal corresponding to a hemodynamic waveform; and
    at least one computer processor connected to the scanner by a wired or wireless connection, wherein the computer processor is adapted to receive the signal for the hemodynamic waveform, determine a Dicrotic Notch using the signal, calculate first and second intrinsic frequencies ($\omega_1$, $\omega_2$) on each side of the Dicrotic Notch for the waveform, and output a signal corresponding to intrinsic frequencies results.

2. A system for acquiring and analyzing a hemodynamic waveform of a subject, the system comprising:
    an ultrasound scanner, the scanner adapted to capture a signal corresponding to a hemodynamic waveform; and
    at least one computer processor connected to the scanner by a wired or wireless connection, wherein the computer processor is adapted to receive the signal for the hemodynamic waveform, determine a Dicrotic Notch using the signal, calculate first and second intrinsic frequencies ($\omega_1$, $\omega_2$) on each side of the Dicrotic Notch for the waveform, and output a signal corresponding to intrinsic frequencies results.

3. A system for acquiring and analyzing a hemodynamic waveform of a subject, the system comprising:
    a tonomeric scanner, the scanner adapted to capture a signal corresponding to a hemodynamic waveform; and
    at least one computer processor connected to the scanner by a wired or wireless connection, wherein the computer processor is adapted to receive the signal for the hemodynamic waveform, determine a Dicrotic Notch using the signal, calculate first and second intrinsic frequencies ($\omega_1$, $\omega_2$) on each side of the Dicrotic Notch for the waveform, and output a signal corresponding to intrinsic frequencies results.

4. A system for acquiring and analyzing a hemodynamic waveform of a subject, the system comprising:
    a microwave scanner, the scanner adapted to capture a signal corresponding to a hemodynamic waveform; and
    at least one computer processor connected to the scanner by a wired or wireless connection, wherein the computer processor is adapted to receive the signal for the hemodynamic waveform, determine a Dicrotic Notch using the signal, calculate first and second intrinsic frequencies ($\omega_1$, $\omega_2$) on each side of the Dicrotic Notch for the waveform, and output a signal corresponding to intrinsic frequencies results.

5. The system of any of claims 1-4, wherein the processor is further adapted to calculate an instantaneous frequency curve for the hemodynamic waveform, and wherein the Dicrotic Notch is determined from the instantaneous frequency curve.

6. The system of any of claims 1-4, wherein the processor is further adapted to calculate a second derivative waveform for the hemodynamic waveform, and determine the Dicrotic Notch is from the second derivative waveform.

7. The system of any of claims 1-4 wherein the result comprises $\omega_1$, $\omega_2$ and $\Delta\omega$.

8. The system of any of claims 1-4, wherein the result comprises an indication of health status of the subject.

9. The system of claim 8, wherein the indication is an alert for hospitalization.

10. A non-transitory computer readable medium having stored thereon instructions, which when executed cause one or more processors to:

receive an input signal corresponding to a hemodynamic waveform;

determine a Dicrotic Notch using the input signal, calculate first and second intrinsic frequencies on each side of the Dicrotic Notch for the waveform; and output a signal corresponding to the intrinsic frequencies.

11. A computer-implemented method of analyzing a signal, comprising:

inputting a hemodynamic waveform data for a subject, the waveform including a Dicrotic Notch;

determining a position of the Dicrotic Notch in the waveform for dividing the signal into first and second sections for analysis;

analyzing each of the first and second sections of the waves by to determine first and second intrinsic frequencies ($\omega_1$, $\omega_2$) where each intrinsic frequency is at or about a frequency that carries the highest energy for all frequencies of an instantaneous frequency curve; and outputting a result of the analyzing.

12. The computer-implemented method of claim 11, wherein the result comprises $\omega_1$, $\omega_2$ and $\Delta\omega$.

13. The computer-implemented method of claim 11, wherein the result comprises an indication of health status of the subject.

14. The computer-implemented method of claim 13, wherein the subject is a human subject.

15. The computer-implemented method of claim 14, wherein the indication is a diagnosis of atrial fibrillation.

16. The computer-implemented method of claim 14, wherein the indication is a diagnosis of heart failure.

17. The computer-implemented method of claim 14, wherein the indication is a diagnosis of aortic valve dysfunction.

18. The computer-implemented method of claim 14, wherein the indication is a diagnosis of arterial disease.

19. The computer-implemented method of claim 18, wherein the arterial disease is selected from aneurysm, stenosis and hypertension.

20. The computer-implemented method of claim 14, wherein the indication is a diagnosis of arrhythmia.

21. The computer-implemented method of claim 14, wherein the indication is an alert for hospitalization.

22. The computer-implemented method of claim 11, wherein the waveform is selected from an arterial pressure wave, a wall displacement wave and a flow or velocity wave.

23. The computer-implemented method of claim 11, repeated in a periodic fashion for monitoring the subject.

24. The computer-implemented method of claim 23, further comprising comparing at least one of $\omega_1$, $\omega_2$ and $\Delta\omega$ for the subject with historical results of at least one of $\omega_1$, $\omega_2$ and $\Delta\omega$ for the subject.

25. The computer-implemented method of claim 11, further comprising comparing at least one of $\omega_1$, $\omega_2$ and $\Delta\omega$ for the subject with non-subject values of $\omega_1$, $\omega_2$ and $\Delta\omega$.

26. The computer-implemented method of claim 11, wherein the results for the subject are logged.

27. The computer-implemented method of claim 11, wherein the waveform data is input from a sensor and the method comprises scanning the subject.

28. The computer-implemented method of claim 26, wherein the sensor is of a type selected from ultrasound, microwave, optical and tonomeric sensors.

29. The computer-implemented method of claim 11, further comprising calculating an instantaneous frequency curve for the hemodynamic waveform, and wherein the Dicrotic Notch is determined from the instantaneous frequency curve.

30. The computer-implemented method of claim 11, further comprising calculating a second derivative waveform for the hemodynamic waveform, and wherein the Dicrotic Notch is determined from the second derivative waveform.

* * * * *